United States Patent [19]

Van den Berg et al.

[11] Plant 4,689

[45] Apr. 14, 1981

[54] IMPATIENS PLANT

[75] Inventors: Cornelis P. Van den Berg; James C. Mikkelsen, both of Ashtabula, Ohio

[73] Assignee: Mikkelsens, Inc., Ashtabula, Ohio

[21] Appl. No.: 103,084

[22] Filed: Dec. 12, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Eclipse, and particularly characterized by the combined characteristics of good self-branching; dark green-red foliage in striking combination with bright orange-red flowers; and excellent keeping quality when grown outside in full sunlight.

1 Drawing Figure

The present invention relates to a new and distinct cultivar of impatiens plant, hereinafter referred to by the cultivar name Eclipse.

Eclipse is the product of a planned breeding program and was originated from a cross made by us in Ashtabula, Ohio. The pollen parent was an unnamed cultivar identified by seedling number 76-396-9, and the seed parent was Satellite, a commercial but unpatented cultivar. Asexual reproduction by terminal or stem cuttings taken by us in Ashtabula, Ohio has shown that the combination of unique characteristics as herein disclosed for Eclipse are stable and retained through successive generations of asexual reproduction.

The following characteristics distinguish Eclipse from both its parent varieties and other cultivated impatiens of this type known and used in the floriculture industry:

1. Eclipse was selected especially for the combination of flower color and foliage color, and the outstanding keeping quality outside in full sunlight.

2. Flower color is bright orange red, more intense than that of Satellite.

3. Flowers appear in an early stage of plant development and plant continues to flower abundantly throughout the growing season.

4. Size of flowers is approximately the same as that of Satellite.

5. Eclipse flowers somewhat later than Satellite.

6. Foliage is dark green-red, with the topside having very short hairs. The texture of the leaf and leaf size are comparable to that of Star War, a commercial but unpatented cultivar.

7. Eclipse has an excellent self-branching habit, comparable to that of Sunfire, a new cultivar of the present inventors and disclosed in pending application Ser. No. 103,090, filed Dec. 12, 1979 and now abandoned.

8. Growth rate of the plant is medium, comparable to that of Star War and somewhat smaller than the average New Guinea Impatiens.

9. Upright growth habit is similar to that of Star War and Sunfire.

10. Eclipse exhibits excellent keeping qualities if grown outside in full sunlight as tested in Ashtabula, Ohio where it will flower from planting date in early June until frost kills the plant.

The accompanying colored photograph illustrates the flower color and foliage of Eclipse, with the colors being as true as it is reasonably possible to obtain in a colored reproduction of this type.

The following is a detailed description of the new impatiens cultivar based on plants produced under commercial practices in Ashtabula, Ohio both in the greenhouses of Mikkelsens Inc. and outdoors in full sunlight. Color references are made to the Royal Horticultural Society Colour Chart except where general terms of ordinary dictionary significance are used.

Parentage:

A controlled cross of the cultivar Satellite as the seed parent and Mikkelsen seedling number 76-396-9 as the pollen parent.

Propagation:

(A) *Type cutting.*—Short tip cutting with stems up to 2 cm. long.

(B) *Time to root.*—10–12 days at 20° C. summer. 14–16 days at 20° C. winter.

(C) *Rooting habit.*—Abundant, fibrous.

Plant description:

(A) *Form.*—Upright, close internoded, self-branching herb.

(B) *Habit of growth.*—Rate of growth moderate for this type of plant. Vegetative shoots are formed at the lower nodes and flowers at the higher nodes.

(C) *Foliage description.*—Leaves simple; lower leaves opposite, higher leaves in whorls of 3, 4 or 5 and sometimes more. (1) Size: Average full grown leaf 130 mm. long × 35 mm. wide. Full grown leaves have petioles up to 20 mm. long, young leaves very short to no petioles. (2) Shape: Elliptic, apex acute to slightly acuminate, base attenuate. (3) Texture: Leathery, topside with very short hairs, underside glabrous. (4) Margin: Entire, ciliate. (5) Color: Young foliage; top side slightly darker than yellow green 147A; under side greyed purple 183A. Mature foliage: top side yellow-green 147A; underside green, heavily infused with red. (6) Venation: Pinnate.

Flowering description:

(A) *Flowering habits.*—Very floriferous under high light conditions. Flowers are single and occur progressively around the whorl of leaves.

(B) *Natural flowering season.*—Flowering is indeterminate and occurs throughout the year.

(C) *Flower buds.*—Conical, covered with 3 sepals. Upper 2 sepals 10 mm. long × 6 mm. wide, acuminate; lower sepal 16 mm. long × 14 mm. wide, petaloid, asymmetrically funnelform, cuspidate, with a hollow spur, red 53A; very tip green. Spur is 50 mm. long, if full grown.

(D) *Flowers borne.*—One pedicels, color greyed red 179A, 50–60 mm. long.

(E) *Quantity of flowers.*—Up to 2 flowers per leaf, occurring progressively around the whorl of leaves.

(F) *Petals.*—(1) Shape: Top petal heart-shaped with wide base; lower petals heart-shaped. (2) Color: Top side in winter when opening orange-red 33A, fading to red 43B, underside red 40 B-C (3) Number: Five, the four lower petals being united in lateral pairs. (4) Size of petals: Top petal 24 mm. in diameter, 2 middle petals 28 mm. long × 22 mm. wide, 2 lower petals 34 mm. long × 28 mm. wide. Flower up to 60 mm. in total diameter.

(G) *Reproductive organs.*—(1) Stamens: Five in number; lower stamen shorter than the others (a)

Anther: hooded shape, top two anthers red and lower anthers near colorless. (b) Pollen color: cream. (c) Stamens united in an asymmetrical tube, covering the ovary. (2) Pistils (a) Stigma shape: Five pointed star, colorless, but infused with red. (b) Style: very short, dome-shaped; colorless, infused with red. (c) Ovary: 5 celled, size 5 mm. long, color green, apex red striped; explosively dehiscent.

Disease resistance:

No general plant diseases observed to date. However, two dotted spider mite can cause plant injury, and thrips can cause injury and stunting of the growing tip.

We claim:

1. A new and distinct cultivar of Impatiens known by the cultivar name Eclipse, as described and illustrated, and particularly characterized as to novelty by the combined characteristics of good self-branching; dark green-red foliage in striking combination with bright orange-red flowers; and excellent keeping quality when grown outside in full sunlight.

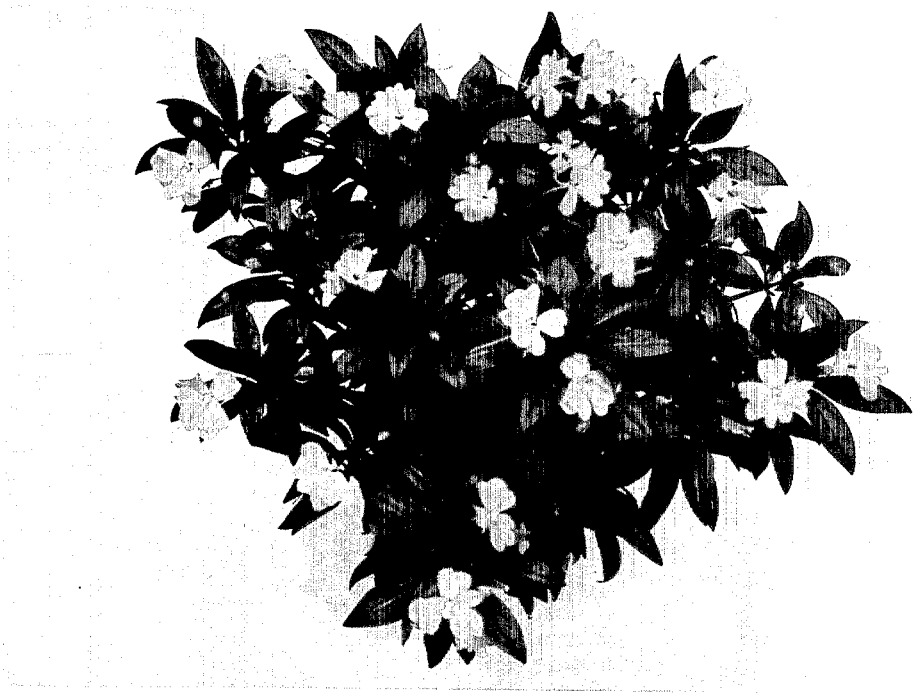

* * * * *